US010420626B2

(12) United States Patent
Tokuda et al.

(10) Patent No.: US 10,420,626 B2
(45) Date of Patent: Sep. 24, 2019

(54) FIDUCIAL MARKERS, SYSTEMS, AND METHODS OF REGISTRATION

(71) Applicants: Canon U.S.A., Inc., Melville, NY (US); The Brigham and Women's Hospital, Inc., Boston, MA (US)

(72) Inventors: Junichi Tokuda, Newton, MA (US); Nobuhiko Hata, Newton, MA (US); Takahisa Kato, Brookline, MA (US); Brian Ninni, Boston, MA (US); Laurent Chauvin, Brookline, MA (US)

(73) Assignees: Canon U.S.A., Inc., Melville, NY (US); The Brigham and Women's Hospital, Inc., Boston, MA (US)

( * ) Notice: Subject to any disclaimer, the term of this patent is extended or adjusted under 35 U.S.C. 154(b) by 184 days.

(21) Appl. No.: 14/755,654

(22) Filed: Jun. 30, 2015

(65) Prior Publication Data

US 2017/0000581 A1 Jan. 5, 2017

(51) Int. Cl.
*A61B 90/00* (2016.01)
*G06K 9/46* (2006.01)
(Continued)

(52) U.S. Cl.
CPC ............... *A61B 90/39* (2016.02); *G06K 9/46* (2013.01); *G06K 9/6218* (2013.01); *G06T 7/75* (2017.01);
(Continued)

(58) Field of Classification Search
CPC .................................................. A61B 90/39
See application file for complete search history.

(56) References Cited

U.S. PATENT DOCUMENTS

| 5,427,099 A | 6/1995 | Adams |
| 5,613,013 A | 3/1997 | Schuette |

(Continued)

FOREIGN PATENT DOCUMENTS

| JP | 2001017422 A | 1/2001 |
| JP | 2006-021016 A | 1/2006 |

(Continued)

OTHER PUBLICATIONS

Frangi, A., et al., "Multiscale Vessel Enhancement Filtering", in Medical Image Computing and Computer-Assisted Intervention MICCAI98 (W. Wells, A. Colchester, and S. Delp, eds.), vol. 1496 of Lecture Notes in Computer Science, pp. 130-137, Springer Berlin Heidelberg, 1998.

(Continued)

*Primary Examiner* — Rochelle D Turchen
(74) *Attorney, Agent, or Firm* — Canon USA Inc. IP Division

(57) ABSTRACT

Exemplary methods, apparatus, and systems are provided for automated detection and registration of medical images using fiducial markers and processing algorithms. By either clustering fiducial markers having a different number, size, shape, configuration, or material property or by using fiducial markers arranged in a ring shape, wherein their arrangement is asymmetric, and then applying a feature extraction to extract the fiducial marker objects, and registering the fiducial marker objects with a model of the fiducial frame, automatic registration can be achieved.

18 Claims, 6 Drawing Sheets

(51) Int. Cl.
*G06K 9/62* (2006.01)
*G06T 7/73* (2017.01)
(52) U.S. Cl.
CPC ............... *A61B 2090/3925* (2016.02); *A61B 2090/3937* (2016.02); *A61B 2090/3954* (2016.02); *A61B 2090/3966* (2016.02); *A61B 2090/3983* (2016.02); *G06T 2207/30021* (2013.01); *G06T 2207/30204* (2013.01)

(56) References Cited

U.S. PATENT DOCUMENTS

| | | | |
|---|---|---|---|
| 6,119,032 | A | 9/2000 | Martin et al. |
| 6,381,485 | B1 | 4/2002 | Hunter et al. |
| 6,975,896 | B2 | 12/2005 | Ehnholm |
| 7,720,522 | B2 | 5/2010 | Solar |
| 8,027,712 | B2 | 9/2011 | Sioshansi |
| 2001/0034480 | A1 | 10/2001 | Rasche et al. |
| 2003/0055410 | A1 | 3/2003 | Evans et al. |
| 2005/0107808 | A1 | 5/2005 | Evans |
| 2007/0122020 | A1 | 5/2007 | Claus et al. |
| 2009/0112082 | A1 | 4/2009 | Piferi |
| 2010/0069746 | A1 | 3/2010 | St. John |
| 2010/0082040 | A1* | 4/2010 | Sahni ............... A61B 17/3403 606/130 |
| 2011/0071389 | A1* | 3/2011 | Simon ............... A61B 6/12 600/426 |
| 2014/0049629 | A1 | 2/2014 | Siewerdsen |
| 2014/0200602 | A1* | 7/2014 | Saad ............... A61B 17/3211 606/172 |
| 2014/0276002 | A1 | 9/2014 | West et al. |
| 2014/0289605 | A1* | 9/2014 | Buelow ............... G06T 7/74 715/232 |
| 2014/0343416 | A1* | 11/2014 | Panescu ............... A61B 34/30 600/431 |
| 2015/0087965 | A1 | 3/2015 | Tokuda |
| 2015/0098636 | A1 | 4/2015 | Bergman |
| 2015/0125890 | A1 | 5/2015 | Wong |
| 2015/0320513 | A1* | 11/2015 | Yoon ............... G06T 7/0012 600/424 |

FOREIGN PATENT DOCUMENTS

| | | |
|---|---|---|
| JP | 2006-141640 A | 6/2006 |
| JP | 2008-000456 A | 1/2008 |
| JP | 2009-233294 A | 10/2009 |
| WO | 2007100293 A1 | 9/2007 |
| WO | 2013/116862 A1 | 8/2013 |
| WO | 2014/152685 A1 | 9/2014 |

OTHER PUBLICATIONS

Fedorov, A., et al., "3D Slicer as an Image Computing Platform for the Quantitative Imaging Network." Magn Reson Imaging, Nov. 2012, pp. 1323-1341, vol. 30, No. 9.

Antiga, L., "Generalizing vesselness with respect to dimensionality and shape", Insight J., Aug. 3, 2007.

Brown, R.A., "A computerized tomography-computer graphics approach to stereotaxic localization", J Neurosurg., Jun. 1979, pp. 715-720, vol. 50, No. 6.

Busse, H., et al., "Method for Automatic Localization of MR-Visible Markers using Morphological Image Processing and Conventional Pulse Sequences: Feasibility for Image-Guided Procedures", J Magn Reson Imaging. Oct. 2007, pp. 1087-1096, vol. 26, No. 4.

De Oliveira, A., et al., "Automatic Passive Tracking of an Endorectal Prostate Biopsy Device Using Phase-Only Cross-Correlation", Magn Reson Med, 2008, pp. 1043-1050, vol. 59.

Dimaio S.P., et al., "Dynamic MRI Scan Plane Control for Passive Tracking of Instruments and Devices", Med Image Comput Comput Assist Interv. 2007, pp. 50-58, vol. 10 (Pt 2).

Fledilius, W., et al., "Robust automatic segmentation of multiple implanted cylindrical gold fiducial markers in cone-beam CT projections", Med Phys., Dec. 2011, pp. 1323-1341, vol. 38, No. 12.

George, A.K., et al., "Robust automatic rigid registration of MRI and X-ray using external fiducial markers for XFM-guided interventional procedures", Med Phys., Jan. 2011, pp. 125-141, vol. 38, No. 1.

Heilbrun, M.P., et al., "Preliminary experience with Brown-Roberts-Wells (BRW) computerized tomography stereotaxic guidance system", J Neurosurg., Aug. 1983, pp. 217-222, vol. 59, No. 2.

Krieger, A., et al., "An MRI-Compatible Robotic System With Hybrid Tracking for MRI-Guided Prostate Intervention", IEEE Trans Biomed Eng., Nov. 2011, pp. 3049-3060, vol. 58, No. 11.

Krishnan, R., et al., "Automated fiducial marker detection for patient registration in image-guided neurosurgery", Comput Aided Surg., 2003, pp. 17-23, vol. 8, No. 1.

Labadie, R.F., et al., "Submillimetric target-registration error using a novel, non-invasive fiducial system for image-guided otologic surgery", Comput Aided Surg., 2004, pp. 145-153, vol. 9, No. 4.

Lorenz, C., et al., "Multi-scale Line Segmentation with Automatic Estimation of Width, Contrast and Tangential Direction in 2D and 3D Medical Images", 1997. pp. 233-242.

Niederveen, A., et al. "Detection of fiducial gold markers for automatic on-line megavoltage position verification using a marker extraction kernel (MEK)", Int J Radiat Oncol Biol Phys., Jul. 2000, pp. 1435-1442 , vol. 47, No. 5.

Smith, L., et al., "Automatic detection of fiducial markers in fluoroscopy images for on-line calibration", Medical Physics, Jun. 2005, pp. 1521-1523, vol. 32, No. 6.

Tokuda, J., et al., "Configurable Automatic Detection and Registration of Fiducial Frames for Device-to-Image Registration in MRI-guided Prostate Interventions", Med Image Comput Comput Assist Interv., 2013, pp. 355-362, vol. 16, No. (0 3).

Tokuda, J., et al., "Integrated navigation and control software system for MRI-guided robotic prostate interventions", Comput Med Imaging Graph., Jan. 2010, pp. 3-8, vol. 34, No. 1.

Tokuda, J., et al., In-bore setup and Software for 3T MRI-guided Transperineal Prostate Biopsy:, Phys Med Biol., Sep. 21, 2012, pp. 5823-5840, vol. 57, No. 18.

Wang, M.Y., et al.,"An Automatic Technique for Finding and Localizing Externally Attached Markers in CT and MR Volume Images of the Head", IEEE Trans Biomed Eng., Jun. 1996, pp. 627-637, vol. 43, No. 6.

Sato, Y., et al., "Three-dimensional multi-scale line filler for segmentation and visualization of curvilinear structures in medical images", Medical Image Analysis, 1998, pp. 143-168, vol. 2, No. 2.

Zheng, G., et al., "Robust automatic detection and removal of fiducial projections in fluoroscopy images: An integrated solution", Med Eng Phys., Jun. 2009, pp. 571-580, vol. 31, No. 5.

Notification of Reasons for Refusal dated Feb. 12, 2019 issued in related JP Patent Application No. 2017-568186 with machine translation.

* cited by examiner

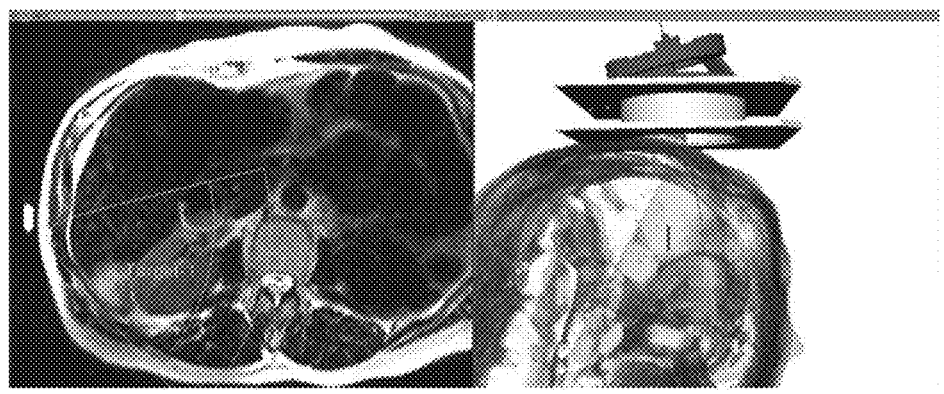
Fig. 3a    Fig. 3b
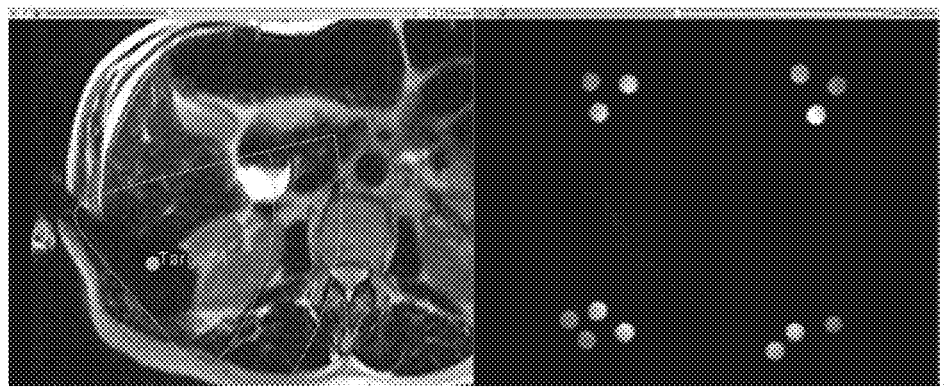
Fig. 3c    Fig. 3d
Figs. 3a – 3d

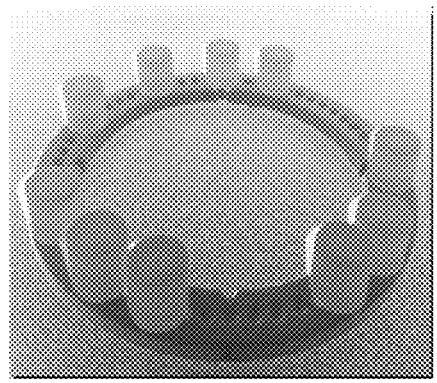 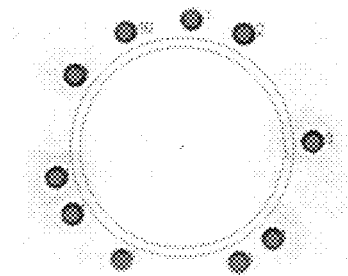
Fig. 4a  Fig. 4b
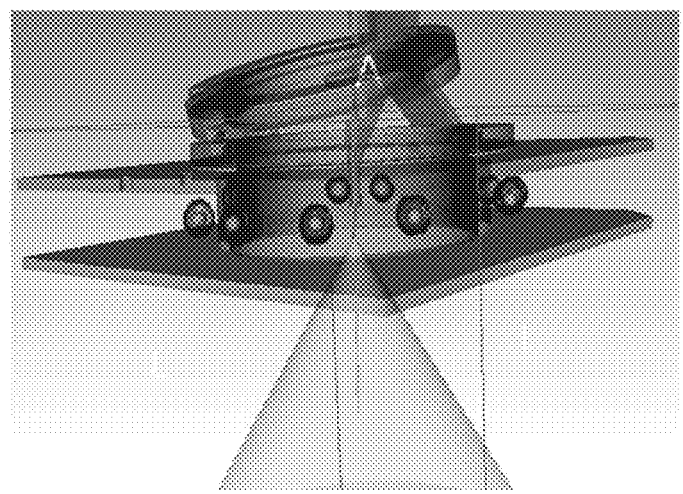
Fig. 4c

FIDUCIAL MARKERS, SYSTEMS, AND METHODS OF REGISTRATION

FIELD OF THE DISCLOSURE

The present disclosure relates generally to systems, methods, and devices for medical imaging and, more particularly to automated detection and registration of medical images using fiducial markers and processing algorithms.

BACKGROUND INFORMATION

Image-guided percutaneous tumor ablations are widely practiced to treat cancers such as liver and kidney cancers. Those therapies include cryoablation, radiofrequency ablation (RFA), microwave ablations (MWA), laser ablations, and irreversible electroporation (IRE). Some imaging modalities that are useful include ultrasound imaging, computed tomography (CT), and magnetic resonance imaging (MRI).

While ultrasound and CT are often imaging modality of choice for guiding probes into the target lesion and monitoring the therapeutic effect, MRI can be preferable as ionizing radiation is not used and a tumor may not present distinctive contrast against the surrounding tissue in the other modalities. Intraprocedural MRI can provide high-resolution 2- or 3-dimensional images with superior soft tissue contrast. Furthermore, MRI offers unique advantage in monitoring of thermal effects during ablation therapies: in cryoablation, formation of the "ice ball" can be monitored as signal void on MR images; in RFA, MWA, and laser ablations, MR thermometry based on proton resonance frequency (PRF) shift method enables monitoring the thermal dose in the tissue. The combination of MRI's capabilities to delineate the tumor and monitor the thermal effect enables physicians to ensure the sufficient ablation margin during the procedures, and hence it potentially leads to reduce tumor recurrence. In addition, MRI does not expose the patient and the clinical staffs to ionizing radiation.

Despite those advantages in target localization and treatment monitoring, the MRI-guidance imposes a technical challenges; a typical MR gantry does not give physicians an easy access to the patient at the isocenter, where images are acquired. Therefore, patient needs to be moved out from the gantry for the probe placement, and moved back into the gantry for imaging. This move-in-and-out approach inhibits the physicians from visually checking the probe location with respect to the target while inserting it unlike other imaging modalities such as ultrasound and CT fluoroscopy. One solution is to treat the patient in an open-configuration scanner. Open-configuration scanners allow physicians access the patient during the scan. However, open-configuration scanners have not become a mainstream, because of the limited imaging capability compared to the conventional closed-bore scanners.

Another solution is to guide the probe using a probe-guide device. The probe-guide device can maintain the probe trajectory mechanically outside the MRI scanner. Therefore, the probe can be inserted into the target as long as the target location remains unchanged. Such devices can be categorized as either "table-, gantry-, and floor-mounted" systems or "patient-mounted" systems depending on how the devices are fixed. The patient-mounted systems are directly attached to the patient's skin rather than the room (or the image coordinate system), hence one can hypothesize that the systems are less vulnerable to the motion of the patient than the other category of the devices. Furthermore, the patient-mounted systems can achieve probe guidance with relatively simple mechanism, because they are designed to be mounted at the probe entry point on the skin, and only need a mechanism to angulate the probe about the entry point.

Thus, there is still a need to accurately place the device on the patient relative to the treatment area. Further, even with a patient-mounted system, patient motion still must be accounted for. Both the body surface and the internal organ can move independently, and cause displacements of the device and the target lesion. Given that imaging for planning and probe placement takes place at different time points in the operation, there is a need to keep track of the displacement of the device due to the motion of the body throughout the operation.

Despite the fact that fiducial markers are an integral tool used to facilitate, automated methods for registering images or assisting in therapeutic planning using the fiducial markers are still limited and error prone when used to provide accurate placement and patient motion. It would therefore be desirable to provide a system and method for automating image analysis and image registration that does not suffer from the drawbacks described above.

SUMMARY OF EXEMPLARY EMBODIMENTS

According to at least one embodiment of the invention, there is provided an apparatus comprising a method of automatic registration. This method comprises the steps of (1) obtaining image data of a medical device, (2) detecting fiducial marker objects within the image data, and (3) registering the fiducial marker objects with a model of the fiducial frame. The medical device involved in the registration comprising a plurality of fiducial markers arranged as a fiducial frame on the medical device, the fiducial frame comprising either at least two clusters of fiducial markers, each cluster comprising a different number, size, shape (e.g., spheres, prolate ellipsoid, oblate ellipsoid, tri-axial ellipsoids, cylinders, tubes, etc.), configuration, or material property (e.g., alloys with differing magnetic field responses) of fiducial marker(s); at least three fiducial markers arranged in a ring shape, wherein their arrangement is asymmetric; or a combination.

The step of detecting fiducial marker objects within the image data comprises the steps of applying a feature enhancement to enhance the fiducial marker objects and applying a feature extraction to extract the fiducial marker objects, where the first step may be omitted in embodiments where the robustness of the feature extraction step is not required. For clustering embodiments, this step also comprises applying a clustering algorithm to define clusters of fiducial marker objects. A representative point for each fiducial marker object or for each cluster of fiducial marker objects is then defined.

The step of registering the fiducial marker objects with a model of the fiducial frame, the step comprising: point to point matching of the representative points. For the ring-shaped embodiment, the step also comprises rotating the ring shape until the representative points of the fiducial marker objects match the model of the fiducial frame (and then performing the point to point matching).

There is also provided a system comprising: a medical device comprising a fiducial frame, wherein the fiducial frame comprising either at least two clusters of fiducial markers, each cluster comprising a different number, size, shape, configuration, or material property of fiducial marker(s); at least three fiducial markers arranged in a ring shape, wherein their arrangement is asymmetric; or a combination. The system also comprises a non-transitory computer-readable storage medium storing a computer-executable program for performing a method of fiducial registration. The method of fiducial registration comprises: detecting fiducial marker objects within the image data and registering the fiducial marker objects with a model of the fiducial frame.

There is also provided an apparatus for use with tomography comprising a medical device and a plurality of fiducials markers arranged as a fiducial frame on the medical device, the fiducial frame comprises at least two clusters of fiducial markers, each cluster comprising a different number, size, shape, configuration, or material property of fiducial marker. In some embodiments, there are at least three clusters of fiducial markers.

In some embodiments, the apparatus is configured such that the fiducial markers are removably attached to form the fiducial frame on the medical device such that the configuration of fiducial markers can be arranged, for example, as easily as moving markers with an extending rod into different holes in the medical device or placing the fiducial markers into different divots on the medical device.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIGS. 3a-3d are images from a graphical user interface of navigation software presenting the relationship between the needle-guide robot, and the patient in 2D and 3D representations. The interface also shows the range that can be targeted with the robot at the current position.

FIGS. 4a-4c show an exemplary configurable fiducial frame having a ring shape. FIG. 4a is an image of a configurable fiducial frame containing fiducials. FIG. 4b is an MR image of the frame of FIG. 4a and FIG. 4c is a 3D representation of a model of a needle guide device containing the fiducial frame.

Figure 1:
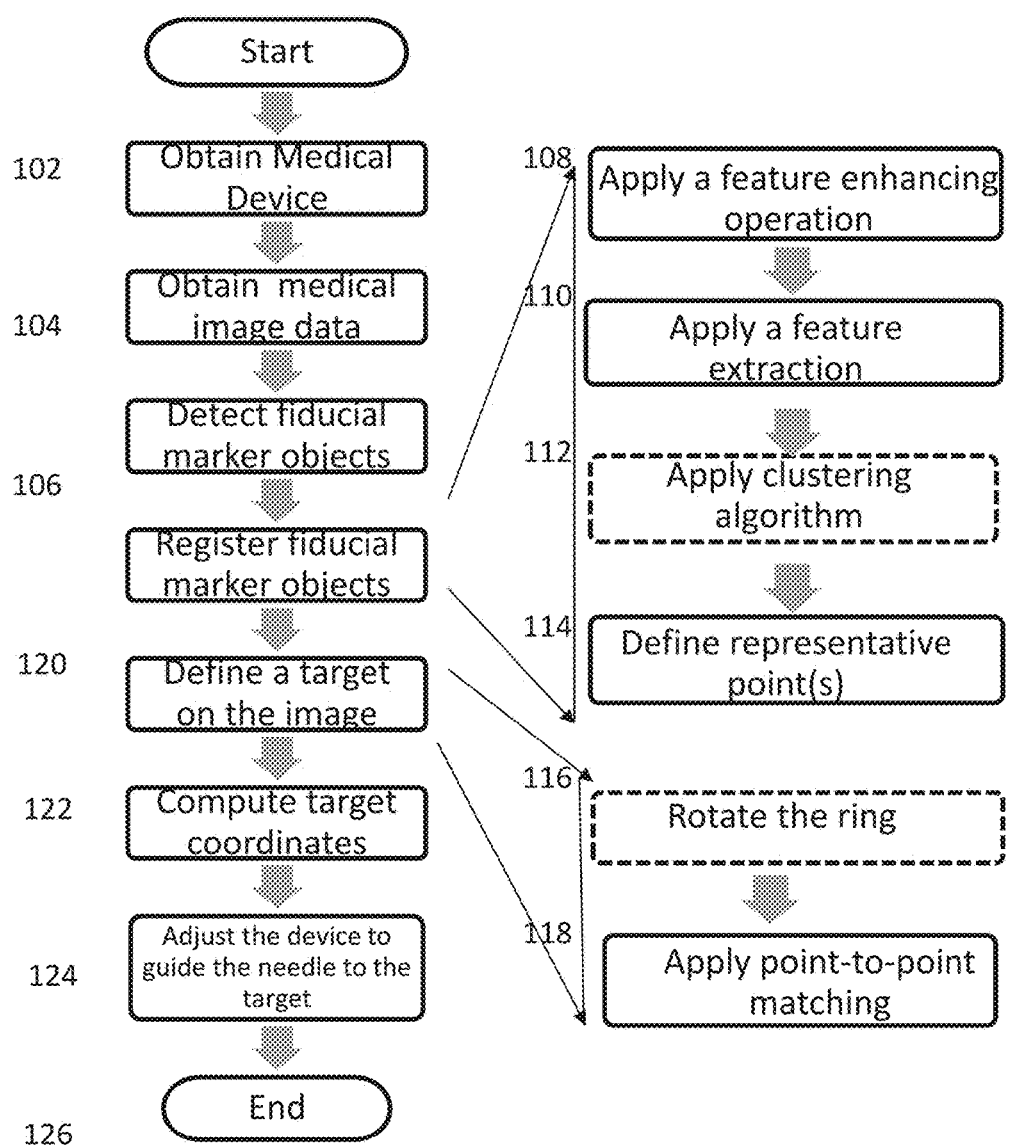
FIG. 1 is a flow chart setting forth the steps of an example process for automatic image processing in accordance with one aspect of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

The embodiments are based on the object of providing fiducial markers, system and methods, including a software system that can adaptively compensate the displacement of the device due to the patient motion using image-based automatic device registration. The system includes a medical device that is patient-mounted and can, for example, direct or position a needle for entry into a patient, a tomographic imaging devices, and navigation software. The navigation software retrieves images from the imaging device and can help clinicians to, for example, determine the needle insertion path on the images, and sends it to the needle guide device.

I. Imaging and Medical Devices

The fiducial markers, system and methods as described herein may be used with any medical device used in conjunction with any tomographic imaging. The tomographic imaging can be, for example, MRI, CT, or ultrasound. The medical device may be a patient mount device such as, for example, a needle placement device.

On example of a medical device that may be used in combination with the present invention is described in U.S. Pat. Pub. 2014/0275979, herein incorporated by reference in its entirety. This reference provides an MRI-compatible body-mount needle guide device with double-ring mechanism.

Other medical devices that may use the fiducial markers, systems, and methods as described herein include other free standing or patient-mounted medical devices for needle placement or for tool placement in assisting diagnosis or surgery. For example, a needle guide template, which consists of a grid of holes, is often used to direct a needle into a foci in image-guided prostate biopsy and brachytherapy.

The fiducial markers, systems, and methods as described herein may also be used outside of the medical industry. For example, in some embodiments, a three dimensional tracking sensor used in motion capture devices, such as in creating realistic computer graphics models for a film.

An embodiment of the system and methods as described herein is described in FIG. 1. First the medical device is obtained 102. The obtaining of the medical device may also include, for example, placing or securing onto a patient over a surgical site. Next, medical image data is obtained of the device and the patient 104. This image date is, for example, MRI or CT data. The fiducial markers objects from the medial image data are then detected 106. To do this, first a feature enhancement 108, such as a derivative-based operation is applied to the data 108. Next, feature extraction is applied 110. When the fiducials are arranged as clusters, a clustering algorithm is applied 112. This step (as indicated by the dashed line) is not used in embodiments where the fiducials are arranged in a ring shape. Representative points are then defined 114. The next step involves registering the fiducial marker objects 120. For embodiments where the fiducials are arranged in a ring shape, the ring is rotated or flipped 116. This may be a full or partial rotation or a 180° flip. Then, a point-to-point matching is applied 118. From the data in the point-to-point matching, a target on the image is defined 122. The target coordinates are computed with respect to the device based on the registration 124. Then, the device is adjusted to guide the needle to the target.

II. Robot Control Software

Figure 2:
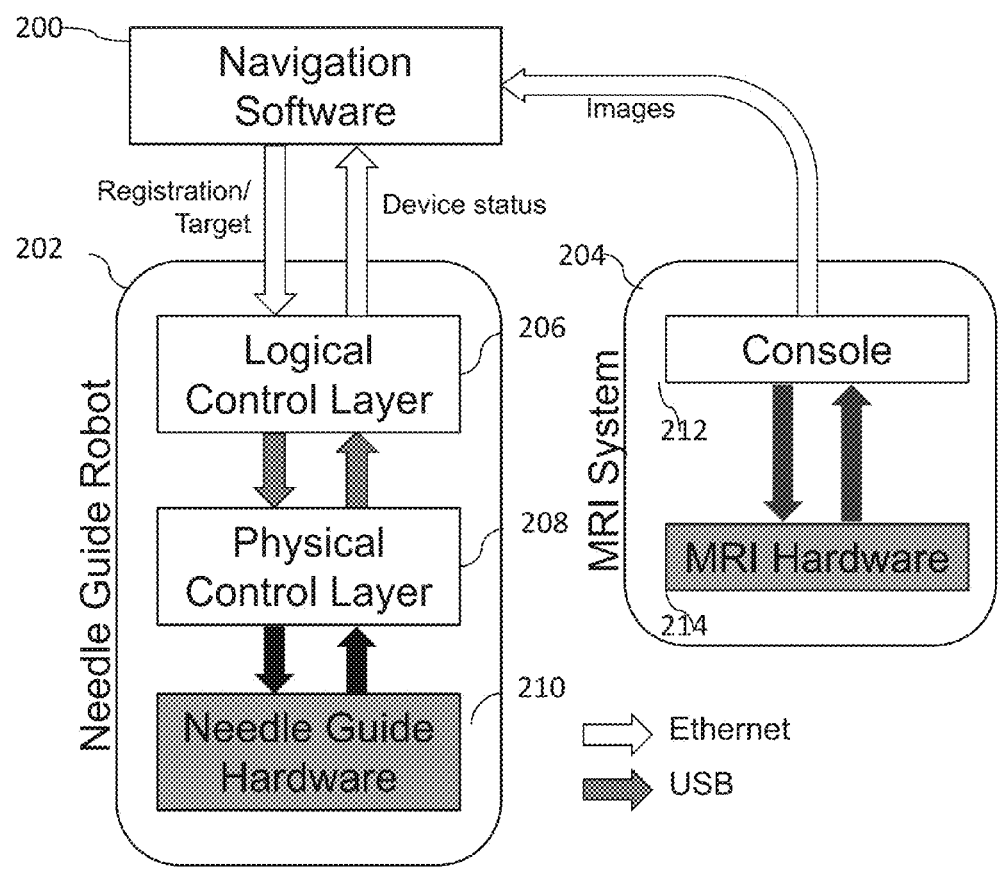
FIG. 2 is a system diagram of needle guide robot system consisting of navigation software, needle guide robot, and MRI scanner.

In some embodiments, a software system is provided that has three layers of components including, navigation software 200, logical control layer 206, and physical control interface 208 (FIG. 2). Those components are implemented as independent software processes, and communicate with each other via, for example, Ethernet and Universal Serial Bus (USB). However, in other embodiments, two more of these components are integrated into a single software process.

The details of those three components are as follows:

Navigation Software

The navigation software 200 is the top layer component in the system and is exemplified in FIG. 2. The navigation software 200 works, for example, as a primary user interface for the physician and/or operator. It is implemented is described herein as a plug-in module for 3D Slicer, open-source medical image computing software [Gering 2001, Andriy 2012] and, through this or other software, received images from the MRI system 204 which includes both the console 212 and MRI hardware 214. The navigation software 200 assists the physician in performing the following tasks.

Needle Placement Planning.

The physician can define a trajectory of needle placement by specifying the targets and skin entry point on the planning image. The software displays a section of the planning image along any plane and allows the physician to specify the points by clicking on it with a mouse. Once the trajectory has been defined, it can reslice the 3D image with a plane along the trajectory so that the physician can find any critical structures and obstacles around the path (FIGS. 3a-3d). The defined trajectory is transferred to the robot control server. The final decision to move the actuator, however, is preferably made by the physician standing by the gantry; the actuators can be powered on only when the physician presses down the footswitch.

Device-to-Image Registration.

The software can automatically detect the markers embedded in the device in the calibration image for the registration of the device to the image coordinate system. Detail of an algorithm of an embodiment of the invention that detects and registers the fiducial markers is described in the following section. Once the device is registered, the software overlays the model of the device and its accessible range on the image, so that the operator can confirm that the all targets are in the range (FIGS. 3a-3d). The linear transformation matrix is transferred to the robot control server over the network using, for example, the OpenIGTLink protocol [Tokuda 2009].

Monitoring and Confirmation of Probe Placement.

The software can be used to visualize the current position and orientation of the device with a 3D model overlaid on the images anytime during the procedure (FIG. 3b). In addition, it also can display confirmation images that shows the probe inserted into the patient with the planned trajectory and target (FIG. 3c). Those features allow the physicians to monitor the device and confirm the probe placement.

Logical Control Layer

The Logical Control Layer (LCL) 206 sits in the middle layer of the system and interfaces the navigation software 200 and low-level physical control layer (PCL) 208. This layer 202 can encapsulate the hardware and the kinematic structure of the device, and to provide a device-independent application program interface (API) to the upper layer. Therefore, LCL 206 consists of the following subcomponents:

TCP/IP Network Interface to the Upper Layer.

Through this interface, the LCL receives commands to the hardware from the upper layer including the target position, and provides the current status of the hardware to the upper layer including the current position of the needle guide, and the status of the device. It also provides the required needle insertion depth as a result of kinematics computation (see Kinematics engine below) to the upper layer. A unique feature of this interface is that LCL provides a configuration of the fiducial frame to the upper layer, where fiducial-based device-to-image registration is performed, keeping the upper layer independent from the hardware. The network interface of this embodiment is compliant with the OpenIGTLink protocol [Tokuda 2009], and thus it can communicate with virtually any software compatible with OpenIGTLink.

Kinematics Engine.

The hardware-independent commands received from the upper layer can then be translated into the target positions of individual actuators based on the kinematics of the needle guide device, and sent to the PCL. The current positions of individual actuators in this embodiment, on the other hand, received from the PCI is translated to the position and orientation of the needle guide and sent to the upper layer.

Serial Interface to the Lower Layer.

The LCL communicates with the lower layer subcomponent through a universal serial bus (USB). Through this exemplary interface, target positions of individual actuators and other device-specific commands are sent to the PCL 208, while the current status of the device and the encoder readings of individual actuators are sent to the LCD. The information exchanged through this interface is dependent on the kinematic structure, but independent from the physical hardware (e.g. motor drivers and encoders).

Physical Control Layer

The role of the Physical Control Layer (PCL) 208 is to provide interface that is independent from the physical input/output (I/O), but dependent on the kinematic structure. In some embodiments, the PCI runs on a Linux-based embedded computer equipped with a USB interface for the communication with the device control server, and a digital input/output interface for reading inputs from encoders and foot switch and giving the target speeds of individual motors to the motor drivers. Once the controller receives target positions for individual actuators, it performs closed-loop PID control of individual motors to position the two rings at the designated positions. Throughout this process, the PCL can optionally keep sending the current positions of the rings and other device status.

III. Fiducial Frame

The fiducial frame contains a plurality of fiducial markers. The markers may all be the same shape and size, such as all being spherical markers, or the fiducial frame may contain fiducial markers having varying sizes and/or shapes. The placement of the fiducial markers within the fiducial frame is either in a ring shape or in two or more clusters. If arranged in a ring shape, the fiducial markers are arranged asymmetrically. If arranged in clusters, the clusters each have a different number, size, shape, configuration, or material property of fiducial marker(s). If the clusters have directionality, there must be at least one cluster such that the directionality of the cluster allows the cluster to be fixed in six degrees of freedom (6DOF). For clusters that have directionality that only allows the clusters to be fixed in less than 6DOF, then there must be at least two clusters. If the clusters do not have directionality, there must be at least three clusters. In some embodiments, there are 2, 3, 4, 5, 6, 7, 8, 9, or 10 clusters. In some embodiments, where the medical device has four corners, there are four clusters that are generally positioned at the corners of the device In some embodiments, all fiducial markers in a cluster are in the same plane. The clusters do not need to have the same number of fiducial markers in the different clusters. There may be 1, 2, 3, 4, 5, 6, 7, 8, 9, 10, 11, 12, 13, 14, 15 or more fiducial markers per cluster. The maximum number of fiducial markers per cluster and also the maximum number of clusters is limited by the relative size of the fiducial markers and clusters to the size of the medical device (e.g., a match-box sized object would not realistically have dozens of marble-sized clusters since this would make the object too ungainly). The number of clusters can be selected based on the desired accuracy of the registration needed for the medical device, where more clusters provide higher accuracy. In some embodiments, particularly in embodiments where different shaped fiducial markers are used, a plurality of spherical fiducial markers is used.

In some embodiments, the medical device or a part of the medical device is manufactured to allow for configurable clusters. For example, a medical device may have multiple divots or holes that are either equally or randomly spaced around a ring or at each edge of the device. Then, when registration of the device is required, fiducial markers are placed in either the divots or holes (if holes, the fiducial marker may have a pin-shaped protrusion that fits into the hole; other formats of removable securing the fiducial markers to the medical device are also contemplated). The number of fiducial markers and number of clusters created can be defined based on the required quality of registration required for the particular application. FIG. 4a is an example implementation of fiducial frame having a ring shape and asymmetrically arranged fiducial markers where the ring-shaped part of the medical device also allows for configurable clusters. The frame consists of 10 identical cylindrical liquid containers attached to a circular template; the template has 60 holes at every 6 degrees along a circle with a diameter of 110 mm allowing different configuration of markers. Each liquid container is fabricated by 3D printing, and has a spherical cavity with a diameter of 10 mm and filled with gadolinium-diethylenetriamine pentaacetic acid (Gd-DTPA) solution. Since the solution appears as a bright spherical object on T1-weighted MR images, the filled container works as a marker. FIG. 4b is an MR image of the frame along the plane parallel to the circle, and the center points of the markers detected by the marker detection algorithm described herein. FIG. 4c is a 3D representation of the model of the needle guide device, the spherical markers, and the detected center points.

Spherical Fiducial Markers

Figure 5A:
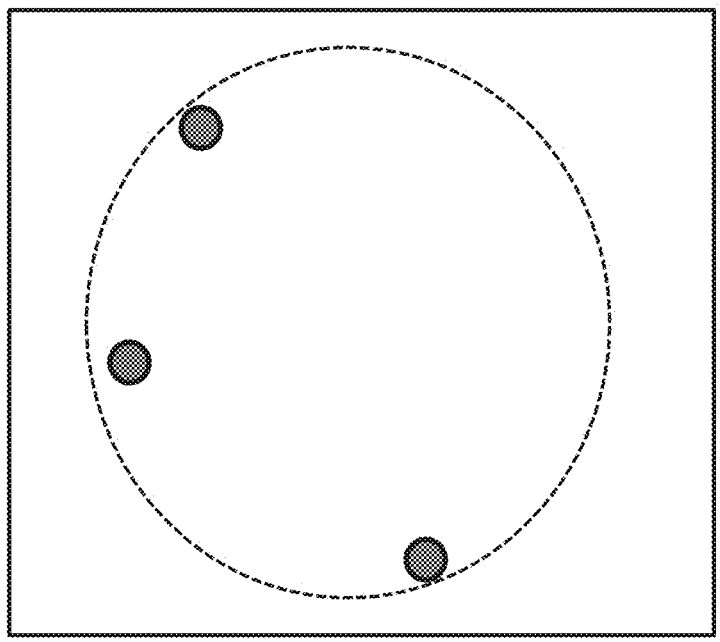
FIGS. 5a-5b are diagrams of exemplary fiducial frames having a ring shape and asymmetrically arranged fiducial markers.
Figure 5B:
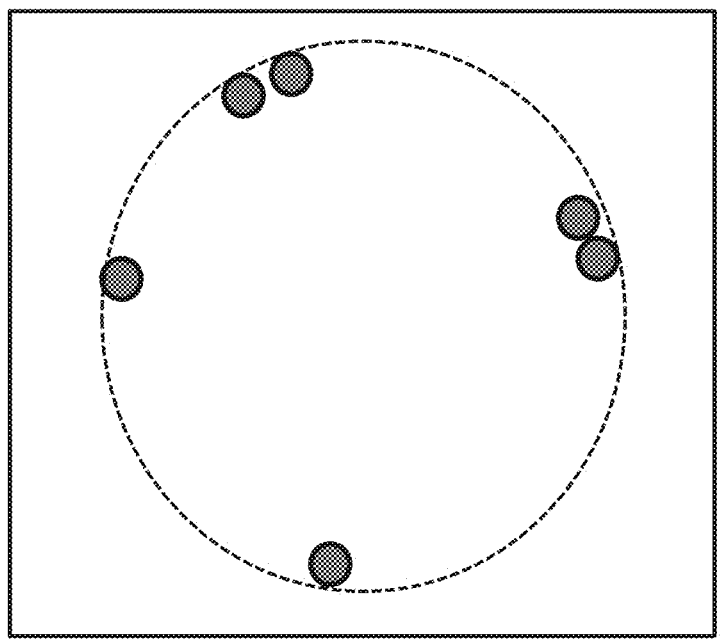

On embodiment of the invention described herein includes the use of spherical fiducial markers. The algorithm for this embodiment relies on a spherical shape of individual fiducial marker with specific diameter $d_M$, and a circular configuration of the fiducial marker (e.g., ring-shaped). This is exemplified in FIGS. 5a and 5b. The spherical shape image date can be detected easily by means of image processing. Also, spherical markers can be easily manufactured. Exemplary spherical fiducial markers are 3D-printed spherical liquid container filled with Gd-DTPA solution.

The spherical markers are aligned in a 2D circle with a predefined diameter $D_F$, but with irregular spacings so that the configuration is asymmetric, meaning that the fiducial frame does never look the same, after rotating about the center and/or flipping the circle. Given the origin of the fiducial coordinate frame defined at the center of the circle, and its z-axis perpendicular to the circle, the coordinates of the i-th marker can be defined as follows:

$$x_i = \left(\frac{d_M}{2}\cos\theta_i, \frac{d_M}{2}\sin\theta_i, 0\right) (i = 1, \ldots, N_M, \theta_1 = 0, \theta_{N_M} < 2\pi)$$

where $N_M$ is the number of spherical markers.

A simple way to achieve the asymmetry requirement is to fulfill the following condition:

$$\delta_i \neq \delta_j \ (0 \leq i < j \leq N_M)$$

where $\delta_i$ is the angle between mark i and i+1 about the center of the circle:

$$\delta_i = \theta_{i+1} - \theta_i \ (1 < i < N_M - 1)$$

$$\delta_N = 2\pi - \theta_N$$

While the fiducial markers for some embodiments are spherical, the term is not meant to imply a perfectly spherical form. Instead, the amount of error in the spherical shape should not be great enough to compromise the ability of the algorithms as described herein below to define the fiducial markers as having a spherical shape and applying an enhancement of the object.

Clustering Detected Markers and Identification of Clusters

Our fiducial-based registration strategy requires each fiducial marker be visible in the tomographic image and have spherical shape, which can be easily enhanced and detected as described herein. Those spherical markers are arranged to form at least three clusters. To simplify the clustering, we define a cluster in such a way that the distance between any given two markers in the same cluster is equal or less than $L_c$, while the distance between markers in different clusters is greater than $L_c$ mm. Given the position of the j-th marker in the i-th cluster $p_{ij}$, $$\|p_{ij} - p_{kl}\| \leq L_c, \text{ where } i = k$$

$$\|p_{ij} - p_{kl}\| > L_c, \text{ where } i \neq k \quad (1)$$

The number of fiducial markers in each cluster is unique, so that the cluster can be identified easily by counting the identified markers in it.

Prior knowledge about the configuration of the fiducial markers defined in Equation (1) to cluster the detected fiducial markers. Given the number of clusters $N_C$ and the maximum distance between points in the same cluster $L_C$, the detected points $p_1, p_2, \ldots, p_n$ are clustered into $C_1, \ldots, C_{N_C}$ in the following steps:

1. Assign $p_1$ to $C_1$, and let the index of the current point i=2.
2. Calculate the distance between $p_i$ and the first points of each cluster (if the first point has been assigned already). If the distance between $p_i$ and the first point of cluster $C_j$ is less than $L_C$, assign $p_i$ to $C_j$. If none of the clusters has the first point located within $L_C$ from $p_i$, assign $p_i$ to one of clusters where no point has been assigned.
3. Increment i by 1. If i≤n, repeat step 2.

By the end of those steps, all points should have been assigned to clusters $C_1, \ldots, C_{N_C}$.

Because we configured the fiducial markers so that each cluster has the unique number of fiducial markers, each cluster can be identified based on the numbers of points assigned to it.

Alternatively, other well-known clustering algorithms used in cluster analysis may be used. For example, hierarchical clustering or k-means clustering may be used. In hierarchical clustering, the algorithm begins with clusters with one point, and progressively merges them based on the distance between the distances between the clusters until the number of clusters became the predetermined number. The k-means clustering partitions the detected points into a given number of clusters, so that the "within-cluster sum of squares" is minimized. The within-cluster sum of squares is defined as the sum of square distances between each point and the nearest mean of points in each cluster.

Clustering Fiducial Markers

In some embodiments, the fiducial frame used on a medical device is comprised of clustered fiducial markers. There may be 1, 2, 3, 4, 5, 6, 7, 8, or more clusters. Each cluster is distinguishable from each other cluster since each cluster will have a different number of fiducial markers, different sized fiducial markers, different shaped fiducial markers, fiducial markers arranged in the cluster in a different configuration, or fiducial markers having different material properties.

Figure 6A:
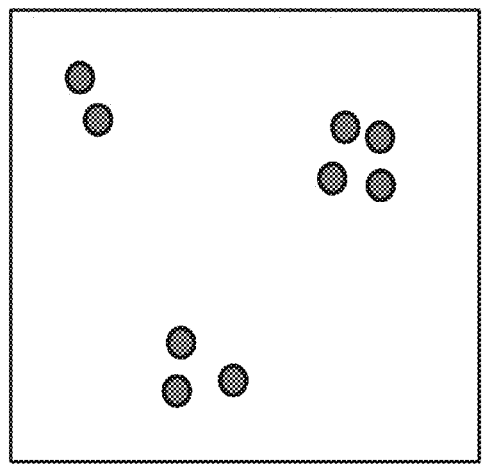
FIGS. 6a-6d are diagrams of exemplary clustered fiducial frames having different number (FIG. 6a), sizes (FIG. 6b), shapes (FIG. 6c) and configuration (FIG. 6d) of fiducial markers in the fiducial frames.

The clusters may contain different numbers of fiducial markers. As exemplified in FIG. 6a, the fiducial frame has three different clusters where each cluster has a different number (2, 3, and 4) of fiducial markers. A cluster may contain a single fiducial marker or it may contain 2, 3, 4, 5, 6, 7, 8, or more fiducial markers. The number is limited only by the relative size of the fiducials as compared to the medical device on which they are placed.

Figure 6B:
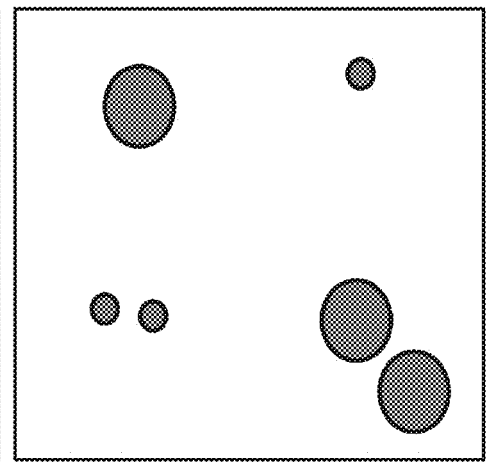

The clusters may contain different sized fiducial. As exemplified in FIG. 6b, the fiducial frame has four different clusters where two clusters have small fiducial markers and two clusters have larger fiducial markers. When multiple sized fiducial markers are used, the fiducial markers must have sufficiently different sizes to be clearly distinguished in the image data.

Figure 6C:
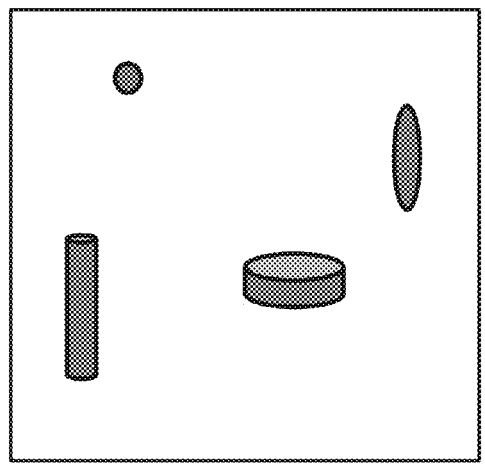

The clusters may contain different shaped fiducials. As exemplified in FIG. 6c, the fiducial frame has four different clusters, where the shape of the fiducial is a sphere, an ellipse (oblate, prolate, or trioaxial), a cylinder, or a tube (e.g., forming a ring, a spiral, etc.). In some embodiments, different shaped cylinders, including tall or short, may be used as distinct shapes.

Figure 6D:
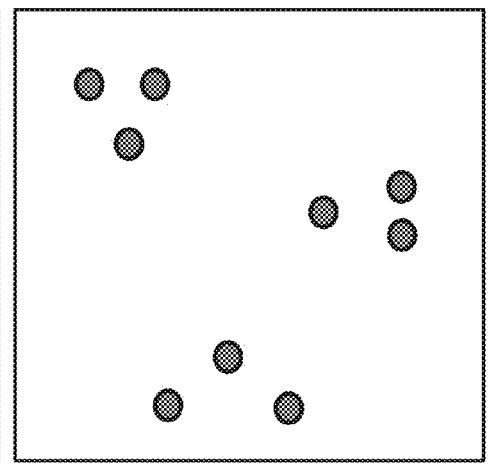

The clusters may be arranged in different configurations. As exemplified in FIG. 6d, three clusters, each having three spherical fiducial markers per the fiducial frame are shown. In this figure, the fiducials of one cluster form an equilateral triangle while the fiducials of the other clusters form an acute and an obtuse triangle. The different configurations do not need to form geometric shapes and can, alternatively, be random. However, the clusters must have their fiducial markers configured such that the different clusters can be distinguished from each other.

The clusters may contain fiducials having different material properties such that the fiducial marker objects are distinguishable in an MRI image or enhanced MRI image. For example, different MRI contrast agents or different concentrations of MRI contrast agents may be used to create the fiducials.

In some embodiments, the clusters may contain two or more of these differences. For example, some clusters could have different sized fiducial markers and other could have different shaped fiducial markers.

N. Detecting Fiducial Markers

Feature Enhancement

One may enhance image objects with the shape of spherical markers to improve the success rate of marker detection by feature extraction in the following step. There are many ways to perform a feature enhancement. One common approach to enhancing the image objects is derivative-based operation, where first or second order spatial derivatives of neighboring voxels are computed to enhance or suppress specific feature of the image.

In some embodiments, the feature enhancement is a derivative-based operation is so called Canny edge detection [Canny, J., *A Computational Approach To Edge Detection*, IEEE Trans. Pattern Analysis and Machine Intelligence, 8(6):679-698, 1986.], where a first-order derivative of a Gaussian is computed at each voxel to extract the edges of objects on the image. After the Canny edge detections, any shapes on the image are contoured and thus can be examined in the following step to detect specific shape.

In some embodiments, the feature enhancement is a derivative-based operation that is the filter proposed by Frangi [Frangi A F, et al., Med. Image Comput. Comput. Interv. (MICCAI'98), Lect. Notes Comput. Sci. Springer Verlag; 1998. p. 130-7]. This is a generalized form of 'vesselness filter' proposed by Sato et al and Lorenz et al; it determines the likelihood that a tube-like, plate-like, or blob-like structure is present at each regions in a gray-scale image based on the eigenvalues of a Hessian matrix [Y. Sato, et al.; Proc. CVRMed-MRCAS'97, LNCS, pages 213-222, 1997; C. Lorenz, et al.; Proc. CVRMed-MRCAS'97, LNCS, pages 233-242, 1997]. In the 'vesselness' function was defined as:

$$V_0(s)=0 \text{ or } (1-e^{-(R_A^2/(2\alpha^2))})e^{-R_B^2/(2\beta^2)}(1-e^{-S^2/(2c^2)}) \text{ if } \lambda_2>0 \text{ or } \lambda_3>0 \quad (2)$$

where s is the scale for the Hessian matrix of the original image at given location x, $\lambda_1$, $\lambda_2$, and $\lambda_3$ are the first, second, and third eigenvalues of the Hessian matrix ($|\lambda_1|\leq|\lambda_2|\leq|\lambda_3|$), S is the Frobenius matrix norm $S=\|H\|_F=\sqrt{\lambda_1^2+\lambda_2^2+\lambda_3^2}$, and $$R_B = \frac{\text{Volume}/(4\pi/3)}{(\text{Largest Cross Section Area}/\pi)^{3/2}} = \frac{|\lambda_1|}{\sqrt{\lambda_2 \lambda_3}} \quad (3)$$

$$R_A = \frac{(\text{Largest Cross Section Area})/\pi}{(\text{Largest Axis SemiLength})^2} = \frac{|\lambda_2|}{|\lambda_3|}. \quad (4)$$

$\alpha$, $\beta$, and c are thresholds that control the sensitivities of the measures $R_A$, $R_B$, and S. The shape and contrast of structures that respond to the vesselness function $V_0(s)$ depend on the relations between the eigenvalues. For example, $V_0(s)$ enhances bright tubular structure, when $|\lambda_1|\approx 0$, $|\lambda_1|<<|\lambda_2|$, $\lambda_2\approx\lambda_3$, $\lambda_2>0$, and $\lambda_3>0$. The size of structures that responds to the function $V_0(s)$ depends on the scale parameter s.

One implementation of the embodiments uses Frangi's approach implemented by Antiga [Antiga 2008] as a C++ class in the Insight Segmentation and Registration Toolkit (ITK). In this implementation, $R_A$ and $R_B$ were further generalized to treat the above mentioned structures as M-dimensional structures in an N-dimensional image (i.e. M=0 for blobs, M=1 for vessels, and M=2 for plates):

$$R_A = \frac{|\lambda_{M+1}|}{\prod_{i=M+2}^{N}|\lambda_i|^{\frac{1}{N-M-1}}} \quad (5)$$

$$R_B = \frac{|\lambda_M|}{\prod_{i=M+1}^{N} |\lambda_i|^{\frac{1}{N-M}}}. \tag{6}$$

When spherical markers are used in the frame, the vesselness function is applied to the image of the fiducial frame with M=0 to enhance bright spherical structures. When tubular markers are used in the frame, the vesselness function is applied with M=1 to enhance them.

In some embodiments, the fiducial marker objects are detected without the step of applying a feature enhancing operation. The step of applying a feature enhancing operation and other object enhancing steps are used to increase the robustness of the feature extraction. However, in some embodiments, there is no need for such an increase in robustness. In such embodiments, feature extraction algorithms may be able to distinguish the markers from other objects without taking this step. Thus, it is contemplated, that in some embodiments, the step of detecting fiducial marker objects within the image data comprises: applying a feature extraction to extract the fiducial marker objects, and defining representative point for each fiducial marker object or for each cluster of fiducial marker objects.

Feature Extraction

Next, the image objects with the shapes of fiducial markers are detected using a shape-based feature extraction.

One example of feature extraction is thresholding, where only the voxels within a given intensity range are extracted as object. This approach is useful, when the range of intensities for the voxels within the marker objects are known, or one can assume that the markers present higher voxel intensities than any other object.

Another example of feature extraction is template matching. In this approach, a small image of the target shape called template image is used. The image similarity between the template image and the given image was evaluated at every point. Points that have high similarities are identified as the center of detected features.

Another example of a feature extraction is a Hough transform. One example of a feature extraction is a Hough transform. Thus, in some embodiments, the object structures enhanced by the vesselness function are then detected by the Hough transform algorithm [Duda R O, Hart P E. Comm. ACM. 1972; 15:11-5]. The Hough transform algorithm is widely used to extract image objects with a specific shape represented by a set of parameters, such as straight lines, circles, and ellipses. The algorithm can be applied to the detection of spherical object in a 3D image.

For spherical objects, the surface of a sphere can be parameterized as:

$$(x-a)^2+(y-b)^2+(z-c)^2=r^2 \tag{7}$$

where, a, b, c, and r are parameters that defines the size and position of the sphere in the 3D image. The first step of the Hough transform algorithm is a voting procedure using a so-called "accumulator space." The dimension of the accumulator space in the detection of spherical object is four, and each point on the accumulator space corresponds to a spherical object in the original image. In the voting procedure, the algorithm examines each point in candidate objects (i.e. high-intensity area) in the original image, and calculates sets of parameters (a, b, c, r) of all the spheres whose surfaces contain the given point. Each parameter set is then mapped as a point into the accumulator space for "voting". Thus, the density of these points at (a, b, c, r) on the accumulator space represents how likely the sphere surface given by (a, b, c, r) contains the high-intensity area on the original image, after all the points are examined; spheres corresponding to the high-density points on the accumulator image are likely the objects to be detected. In our fiducial marker detection, we constrain the r to $r=d_M/2$. After the Hough transform, the position of the center of mass for each spherical object is calculated.

The Hough transform can be used in other embodiments, where objects having analytical shapes that can be represented by parameters. Examples of analytical shapes include ellipse, cylindrical, or other shape is used, the surface of the object can be parameterizes similarly to that described for a sphere. Of course, for some such objects, the number of parameters used must be increased in order to particularly describe the size and position of the object in the 3D image.

Representative Point Definition

For each object or cluster, a representative point is determined. This representative point may be the center of mass. Other methods of defining a representative point are, for example, selecting the uppermost point of each fiducial marker object, calculating a foci, calculating an apex (of a cone, for example), or similar method. Such methods are generally known in the art.

V. Registering Fiducial Markers

The last step discussed in this embodiment of the fiducial marker registration process is matching the model of markers to the detected markers. This step consists of four sub-steps (FIG. 7): 1) fit a 2-dimensional plane to the detected markers; 2) estimate the circle, which the detected markers are aligned to; 3) match the model circle to the estimated circle; 4) find the rotation that matches the model and detected markers. The first sub-step is achieved by principal component analysis (PCA); PCA transforms the points to a new coordinate system, where the greatest variance appears along the first axis, the second largest variance along the second, and the least variance along the third axis. Therefore, the plane fitted to the points is defined by the new coordinate system. Let the coordinates of the detected markers $X=(x_1, x_2, \ldots, x_N)$. The principal component decomposition can be given using a 3-by-3 matrix W:

$$T=\hat{X}W$$

where T is an N-by-3 matrix representing the coordinates of the markers converted to the new space, $\hat{X}$ is an N-by-3 matrix representing the coordinates of the markers shifted so that the empirical mean is zero ($\hat{X}=(x_1-\bar{x}, x_2-\bar{x}, \ldots, x_N-\bar{x})$, where $\bar{x}=\Sigma_{n=1}^{N} x_n/N$). The k-th column of the W corresponds to the k-th eigenvector of $\hat{X}^T\hat{X}$, representing the normal vector for the k-th axis in the new coordinate space. Since the third axis has the least variance, the all markers are in the plane defined by the first and the second axes.

The center of the markers can be estimated by the intersection of the perpendicular bisectors of two chords defined by three different points on the circle. In our implementation, the bisectors calculated from all $_NC_3$ combinations of points are averaged to estimate the center of the markers. Given three markers selected from the detected markers, $P_1$, $P_2$ and $P_3$, the bisecting point of $P_1P_2$ and $P_2P_3$, represented by $M_{12}$ and $M_{23}$ can be obtained by:

$$m_{12}=(p_1+p_2)/2$$

$$m_{23}=(p_2+p_3)/2$$

where $p_1$, $p_2$, and $p_3$ are the 2-dimensional position vectors of $P_1$, $P_2$ and $P_3$. The normal vectors for the perpendicular bisectors of $P_1P_2$ and $P_2P_3$ are:

$$n_{12}=R_{90°}v_{12}$$

$$n_{23}=R_{90°}v_{23}$$

where $v_{12}=p_2-p_1$ and $v_{23}=p_3-p_2$, and $R_{90°}$ is a counter-clockwise rotation about the xorigin by 90 degrees:

$$R_{90°} = \begin{pmatrix} \cos\pi/2 & -\sin\pi/2 \\ \sin\pi/2 & \cos\pi/2 \end{pmatrix}$$

The projection of $M_1$ onto the perpendicular bisector of $P_1P_2$, represented by $H_{12}$ is calculated by:

$$h_{12}=m_{12}+\{(m_{23}-m_{12})\cdot n_{12}\}\cdot n_{12}$$

The intersection of the two perpendicular bisectors, C, can be represented using a scalar parameter a:

$$c=m_{23}+a\cdot n_{23}$$

Since the projection of C onto $M_2H$ must be H, $$a\cdot n_{23}\cdot\frac{(h_{12}-m_{23})}{\|h_{12}-m_{23}\|}=\|h_{12}-m_{23}\|$$

Using this relationship, the scalar parameter a can be calculated as:

$$a=\frac{\|h_{12}-m_{23}\|^2}{n_{23}\cdot(h_{12}-m_{23})}$$

Therefore, $$c=m_{23}+n_{23}\frac{\|h_{12}-m_{23}\|^2}{n_{23}\cdot(h_{12}-m_{23})}$$

The transformation that fits the circle in the model to the detected markers is:

$$T_{c+}(p)=R_{c+}\cdot p+c$$

where $R_+=(w_1^T,w_2^T,w_3^T)$. The circle can also be fitted to the model, after flipping (or rotating about x- or y-axis by 180 degrees). In this case, the transformation is:

$$T_{c-}(p)=R_{c-}\cdot p+c=R_{c+}\cdot R_{x,180°}\cdot p+c$$

where $R_{x,180°}$ is a counter-clockwise rotation about the x-axis by 180 degrees $$R_{x,180°} = \begin{pmatrix} 1 & 0 & 0 \\ 0 & \cos\pi & -\sin\pi \\ 0 & \sin\pi & \cos\pi \end{pmatrix}.$$

The last step is finding the rotation about the axis of the circle that fits the all model markers to the detected markers after transformation $T_{c+}$ or $T_{c-}$. Given an angle for the rotation about the z-axis $\theta$, the final transformation can be described as:

$$T_\theta(p)=R_c\cdot R_z(\theta)\cdot p+c$$

where $$R_c=R_{c+} \text{ or } R_c=R_{c-}=R_{c+}\cdot R_{x,180°}$$

We define a goodness of fit as the mean square distance of closest points between the transformed model markers and the detected markers:

$$E=\frac{1}{N}\sum_{k=1}^{N}\min_j\|q_j-T_\theta(p_k)\|^2$$

Using this goodness of fit, our problem can be described as:

$$\theta=\arg\min_\theta E=\arg\min_\theta\frac{1}{N}\sum_{k=1}^{N}\min_{j\in\{1,\ldots,N\}}\|q_j-T_\theta(p_k)\|^2$$

While $\theta$ is a continuous parameter, we can limit the search space by assuming that one of the transformed model markers always matches one of the detected markers. To match the first model marker to the l-th detected markers:

$$q_l=T_{\theta_{1,l}}(p_1)=R_c\cdot R_z(\theta_{1,l})\cdot p_1+c$$

$$R_z(\theta_{1,l})\cdot p_1=R_c^{-1}(q_l-c)$$

Therefore, $\theta_{1,l}$ is the rotation angle between $p_1$ and $q_l'=R_c^{-1}(q_l-c)$. Using $\theta_{1,l}$, $\theta$ that minimize the goodness of fit E can be rewritten as:

$$\theta=\arg_{\theta_{1,l}}\min_{l\in\{1,\ldots,N\}}\frac{1}{N}\sum_{k=1}^{N}\min_{j\in\{1,\ldots,N\}}\|q_j-T_{\theta_{1,l}}(p_k)\|^2$$

Finally, the registration transform can be computed by substituting the solution $\theta$ to $T_\theta(p)$.

In the real-world application, there are errors in detecting the markers and the subsequent processing steps. To minimize the impact of marker detection errors, the registration matrix is further optimized by point-to-point registration based on the correspondence of markers between the model and the detected markers identified by $T_\theta(p)$.

Registration of the fiducial marker model to the detected fiducial markers consists of cluster-to-cluster matching for initial estimation of registration, and point-to-point matching for refinement of estimated registration. For the cluster-to-cluster matching, the average positions of the fiducial markers for each cluster are calculated for both the fiducial marker model, and the detected fiducial markers. The average positions in the model and the detected fiducial markers are matched using a point-to-point registration algorithm. The point-to-point registration gives an initial estimation of registration matrix. Once the clusters in the model and the detected fiducial markers are matched, individual markers are matched using an iterative closest point (ICP) algorithm. Because the ICP matches the points in the model and the detected fiducial markers by minimizing the distances between them, markers do not need to be identified individually.

VI. Applications

An application for the fiducial markers, systems, and methods as described herein can be applied using a double-ring needle guide device. As described in U.S. Pat. Pub. 2014/0275979, two-DOF RCM motion is achieved by a double-ring mechanism, which consists of two ring-shape rotary stages coupled together with a fixed angle. Those ring-shape stages may be manually rotated or driven by a motor such as an ultrasonic actuator. By rotating the two stages independently, one can rotate the needle guide in two directions about the remote center. The stages also have embedded encoders for the PID control. The target angles of the lower and upper rotary stages $\theta_1$ and $\theta_2$ can be calculated by:

$$\theta_2 = \pm 2\sin^{-1}\left(\frac{|p_n - p_v|}{2r}\right) \quad (1)$$

$$\theta_1 = \tan^{-1}\left(\frac{y_n}{x_n}\right) + \sin^{-1}\frac{\sin\theta_2 |p_n - p_v|}{\sqrt{y_n^2 + x_n^2}} \quad (2)$$

where, r is the radius of the upper rotary stage, $p_t$ is the target position, $p_n$ is the intersecting point of the upper rotary stage and the needle guide axis, and $p_v$ is the intersecting point of the upper rotary stage and the axis of the lower ring. $x_n$ and $y_n$ are the x- and y-elements of $p_n$. The needle insertion depth from the entry of the needle guide is given by:

$$d = |p_n - p_t| \quad (3)$$

Clinical Workflow

An exemplary clinical workflow is described, using the two-ring device described above. In this embodiment, the active 2-DOF mechanism of the two-ring device tilts a passive needle guide about a given skin entry point to align the needle with the trajectory to a lesion, which is identified on a 3D intraoperative image of the patient. A clinical workflow is provided to introduce ablation probes into the target lesion under MRI guidance. Note that the patient can stay on the patient table throughout the procedure, and is moved into the scanner's gantry only when images are acquired; the other steps can be performed outside the gantry:

1. A first 3-dimensional (3D) image (planning image) is acquired and transferred to navigation software.
2. Entry and target points are defined on the navigation software.
3. The needle guide device is mounted on the patient body so that its remote-center-of-motion (RCM) point is provided to the defined entry point.
4. A second 3D image (calibration image) is acquired and transferred to the navigation software.
5. The navigation software automatically detects and localizes the fiducial markers attached to the device.
6. The navigation software sends the spatial relationship between the device and the image coordinate system to the device controller so that the controller can transform the target coordinates from the image system to the device coordinate system.
7. The navigation software sends the coordinates of the target and entry points to the device controller.
8. The device controller drives the actuators to align the needle guide to the designated trajectory.
9. The physician inserts the probe towards the target using the guide, where the targeting is either manual or automated.
10. A 3D image (confirmation image) is acquired to confirm the probe placement.
11. Steps 9 and 10 may be repeated until a plurality of probes is placed properly.

Once the probes are placed at planned positions, cryoablation is performed. The extent of frozen tissue with respect to the target tumor is monitored by MR images acquired throughout the freeze-thaw cycle.

The systems and methods presented herein are described in conjunction with an MRI-compatible body-mount needle guide device with double-ring mechanism described in U.S. Pat. Pub. 2014/0275979, herein incorporated by reference in its entirety. However, the system and methods as described herein may be used with any medical device used in conjunction with any tomographic imaging.

Device-to-Image Registration

We tested our registration algorithm by using simulation and imaging experiments. The goal is to evaluate its accuracy, speed, and robustness of the proposed registration method under various imaging conditions, including different device positions and orientations, spatial resolutions, signal-to-noise ratios (SNR), and configurations of the fiducial markers.

Simulation

A random rigid transform was created by generating three translational parameters (x, y, z) and Euler angles ($\alpha,\beta,\gamma$) with ranges of (−150 mm, 150 mm) for the translational parameters, (−$\pi,\pi$) for $\alpha$ and $\gamma$, and (−$\pi/2$, $\pi/2$) for $\beta$. The matrix representation of the transform is:

$$T = Rp + t$$

where t=(x, y, z) and, $$R = \begin{pmatrix} \cos\beta & -\cos\gamma\sin\beta & \sin\beta\sin\gamma \\ \cos\alpha\sin\beta & \cos\alpha\sin\beta\cos\gamma - \sin\alpha\sin\gamma & -\cos\gamma\sin\alpha - \cos\alpha\cos\beta\sin\alpha \\ \sin\alpha\sin\beta & \cos\alpha\sin\gamma + \cos\beta\cos\gamma\sin\alpha & \sin\alpha\cos\gamma - \cos\beta\sin\alpha\sin\gamma \end{pmatrix}$$

The random rigid transform was then applied to a point set as a model of the fiducial marker. Then, a synthetic 3D raster image of the transform fiducial marker is rendered in a 3D image with a given spatial resolution from the transformed point set. In this rendering step, the partial volume effect was taken into account to calculate the signal intensity of the voxels at the boundary of the markers. The partial volume effect is crucial for the registration algorithm to achieve an accuracy smaller than the voxel size. Finally, a simulated fiducial image is generated by adding noise such as a Gaussian noise with a variable standard deviation to the synthetic 3D image. Once the simulated fiducial image was created, the transform of the fiducial frame was estimated by applying the device-to-image registration to the image. The estimated transform was compared with the original transform used to generate the synthetic image.

Imaging Experiment

The registration algorithm was also evaluated using MR images of the phantom. We created a stage that could place the device and fiducial marker at know position and orientation in the gantry. A 3D MR image was acquired at each position and orientation, performed device-to-image registration using the proposed algorithm to estimate the position and orientation of the device, and then compared those estimations with the position and orientation given by the stage. The images were acquired in a 3T MRI scanner (MAGNETOM Verio, Siemens Healthcare, Erlangen, Germany) with a body matrix coil and a multi-slice T2-weighted Half-Fourier Acquisition Single-shot Turbo spin echo (HASTE) sequence.

Simulation to Evaluate Targeting Error Due to Patient Motion

The possible displacement of the device during the clinical procedures was tested. This movement would be due to the motions of the skin surface and the internal organ by using 3D images acquired during MR-guided cryoablations of the kidney. The images were acquired periodically during the probe placement process, and thus they represent the displacements of those structures. A device placement simulator as used to estimate what the possible position and orientation of the device would have been, if it had been placed at the entry point on the skin.

Imaging Protocol

All images were acquired using the same scanner as the imaging study for the validation of the device-to-image registration. In one embodiment as described herein, multislice T2-weighted MR images were acquired during the probe placement process using the same body matrix coil and the multi-slice 2D MRI.

Estimation of Potential Device and Target Displacements

A specific challenge for the body-mounted device is that the position and orientation of the robot is unknown until it is physically mounted on the patient. As described in section "Clinical Workflow," the device will not be present on the patient while reviewing the planning image. This limitation may cause misplacement of the device, where the targets turns out to be out of the accessible range after being placed. To allow the physician to expect how the device is mounted on the patient, we implemented a simple method to estimate possible position and orientation of the device before physically mounting it on the patient.

Our method is based on a skin entry point planned by the physician, and a 3D surface model of the patient generated from the planning image acquired at the beginning of the procedure. To generate the 3D surface model, the body of the patient in the image is segmented by binarizing the image with a threshold. The surface of the segmented body is then extracted as a polygon model using a marching cube algorithm. Using the surface model and the coordinate of the skin entry point, an area of the patient body that contacts the body-mount device is estimated. In this estimation, we assume that the device contact the skin mostly at the ring-shape inner edge of the base, and the area within the ring is approximately a flat plane. Under those assumptions, the orientation of the device can be approximated by the mean of the normal vectors of the polygons in the area on the skin within the ring. The position of the device is calculated by matching the RCM of the device with the skin entry point while maintaining the orientation.

Each 3D image is analyzed to estimate the potential device and target displacements. The body of the patient was segmented manually by using open-source medical image computation software, 3D Slicer; the image was first binarized with a threshold and then edited with the drawing tool. The segmented image was saved as a label image, and converted to a 3D surface model using a marching cube algorithm. The probe insertion point on the skin was also identified on the original 3D image, and mapped onto the surface model. Based on the probe insertion point and the 3D surface model of the patient body, the possible position and orientation of the device is estimated using the method described in the previous section.

The displacement of the target was analyzed using image registration of the kidney region between the initial image and other images acquired at different time points. We assumed that the motion of the target moved with the kidney, and the motion of the kidney was approximated as rigid registration. To focus on the kidney, it was roughly counted manually to create a mask, and use it to limit the region to evaluate the similarity of the two images. The rigid registration was based on the maximization of mutual information. After all images in the same procedure were analyzed, the displacements of the device from its original position over the course of the needle placement process were calculated. Based on the estimated displacements of the target and the kidney, the relative position of the target with respect to the needle guide device was computed as potential position error.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer may be combined with, for example, an MRI system including MRI hardware and console or may be separate from the imaging system. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

As used herein, "distinguishable" as used in the context of distinguishing clusters of fiducial markers means that the configuration (number, size, shape, configuration, or material property) of the various clusters can be differentiated from each of the other clusters with a certainty of at least to establish one-to-one correspondences between clusters of markers on the physical frame and those detected on the image. Once the clusters are distinguished, one can localize the frame in the image coordinate system.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A method of automatic registration, comprising:
   obtaining image data of a medical device, the medical device comprising a plurality of fiducial markers arranged as a fiducial frame on the medical device, said fiducial frame comprising:
   (a) at least two clusters of fiducial markers, each cluster comprising a different number, size, shape, configuration, or material property of fiducial marker(s), or
   (b) at least three fiducial markers arranged in a ring shape, wherein their arrangement is asymmetric;
   detecting fiducial marker objects within the image data by:
   applying a feature enhancement to the image data to enhance the fiducial marker objects, the feature enhancement including shape data of the fiducial markers,
   applying a feature extraction based on the shape data of the fiducial markers to extract the fiducial marker objects, and
   for image data of the medical device comprising the at least two clusters of fiducial markers, applying a clustering algorithm to define clusters of the fiducial marker objects;
   defining a representative point for each extracted fiducial marker object or for each cluster of fiducial marker objects; and
   registering the fiducial marker objects with a model of the fiducial frame, the registering step comprising:
   (a) for image data of the medical device comprising the at least two clusters of fiducial markers,
      (i) calculating average positions of fiducial markers for each cluster in the model of the fiducial frame,
      (ii) point to point matching of the average positions of the fiducial markers for each cluster with the model of the fiducial frame, and then
      (iii) matching individual fiducial marker objects using an iterative closest point algorithm, or
   (b) for image data of the at least three fiducial markers arranged in the ring shape, estimating a circle to which the fiducial marker objects are aligned and matching a model circle to the estimated circle, the model circle based on model markers included in the model of the fiducial frame, and rotating the ring shape until the representative points of the fiducial marker objects match the model of the fiducial frame.

2. The method of claim 1, wherein the feature enhancement comprises a Hessian matrix.

3. The method of claim 2, further comprising using eigenvalues of the Hessian matrix to enhance the voxels that likely belong to the fiducial marker objects.

4. The method of claim 3, wherein the eigenvalues of the Hessian matrix comprise directionality and define shape information for the fiducial marker objects.

5. The method of claim 1, wherein the feature extraction comprises a Hough transform algorithm.

6. The method of claim 1, wherein defining a representative point comprises calculating the center of mass for each fiducial marker object or cluster of fiducial marker objects.

7. The method of claim 1, wherein the plurality of fiducial markers are spherical.

8. The method of claim 1, wherein the at least two clusters of fiducial markers comprise between one and six fiducial markers per cluster, and wherein each cluster has a different number of fiducial markers.

9. The method of claim 1, having between two and ten clusters of fiducial markers that comprise between two and six fiducial markers per cluster and the spatial arrangement of fiducial markers within each cluster is distinct.

10. The method of claim 9, having three or four clusters.

11. The method of claim 1, comprising at least three clusters of fiducial markers that comprise between one and six fiducial markers per cluster, wherein each cluster comprises at least one fiducial marker having a different size.

12. The method of claim 1, wherein the plurality of fiducial markers comprise at least three of spheres, prolate ellipsoid, oblate ellipsoid, tri-axial ellipsoids, cylinders, and tubes.

13. The method of claim 1, wherein said fiducial frame comprises at least three fiducial markers arranged in a ring shape, wherein their arrangement is asymmetric.

14. The method of claim 13, wherein the medical device further comprises:
a base adapted to be placed on a body surface; and
an opening to provide visual and physical access to the body surface through the medical device, and the fiducial markers are arranged in a ring shape that surrounds the opening in the medical device.

15. The method of claim 1, wherein said fiducial frame comprises at least two clusters of fiducial markers, each cluster comprising a different number, size, shape, configuration, or material property of fiducial marker(s).

16. A system comprising:
a medical device comprising a fiducial frame, wherein the fiducial frame comprises:
(a) at least two clusters of fiducial markers, each cluster comprising a different number, size, shape, configuration, or material property of fiducial marker(s), or
(b) at least three fiducial markers arranged in a ring shape, wherein their arrangement is asymmetric; and
a non-transitory computer-readable storage medium storing a computer-executable program for performing a method of fiducial registration, the method comprising:
obtaining image data of a medical device;
detecting fiducial marker objects within the image data by:
applying a feature enhancement to the image data to enhance the fiducial marker objects, the feature enhancement including shape data of the fiducial markers,
applying a feature extraction based on the shape data of the fiducial markers to extract the fiducial marker objects, and
for image data of the medical device comprising the at least two clusters of fiducial markers, applying a clustering algorithm to define clusters of the fiducial marker objects;
defining a representative point for each extracted fiducial marker object or for each cluster of fiducial marker objects; and
registering the fiducial marker objects with a model of the fiducial frame, the registering step comprising:
(a) for image data of the medical device comprising the at least two clusters of fiducial markers, (i) calculating average positions of fiducial markers for each cluster in the model of the fiducial frame, (ii) point to point matching of the average positions of the fiducial markers for each cluster with the model of the fiducial frame, and then (iii) matching individual fiducial marker objects using an iterative closest point algorithm, or
(b) for image data of the at least three fiducial markers arranged in the ring shape, estimating a circle to which the fiducial marker objects are aligned and matching a model circle to the estimated circle, the model circle based on model markers included in the model of the fiducial frame, and rotating the ring shape until the representative points of the fiducial marker objects match the model of the fiducial frame.

17. The system of claim 16, wherein the medical device further comprises a base adapted to be placed on a body surface and an opening to provide visual and physical access to the body surface through the medical device, and the fiducial markers are arranged in a ring shape that surrounds the opening.

18. A method of automatic registration, comprising:
obtaining image data of a medical device, the medical device comprising a plurality of spherical fiducial markers arranged as a fiducial frame on the medical device, said fiducial frame comprising at least three fiducial markers arranged in a ring shape, wherein their arrangement is asymmetric;
detecting fiducial marker objects within the image data by:
applying a feature enhancement to the image data to enhance the fiducial marker objects, the feature enhancement including shape data of the spherical fiducial markers, and
applying a feature extraction based on the shape data of the spherical fiducial markers to extract the fiducial marker objects;
defining a representative point for each extracted fiducial marker object; and
registering the fiducial marker objects with a model of the fiducial frame, the registering including estimating a circle to which the fiducial marker objects are aligned and matching a model circle to the estimated circle, the model circle based on model markers included in the model of the fiducial frame, the registering step comprising rotating the ring shape until the representative points of the fiducial marker objects match the model of the fiducial frame.

* * * * *